United States Statutory Invention Registration [19]

[11] Reg. Number: H642

Floyd et al. [43] Published: Jun. 6, 1989

[54] SUBSTITUTED URIDO AMINO AND IMINO ACIDS AND ESTERS

[75] Inventors: David Floyd; Melanie J. Loots, both of Pennington, N.J.

[73] Assignee: E. R. Squibb & Sons, Inc., Princeton, N.J.

[21] Appl. No.: 642,278

[22] Filed: Aug. 20, 1984

[51] Int. Cl.[4] ..... C07D 207/00

[52] U.S. Cl. ..... 514/423; 548/533; 548/535; 548/492; 548/407; 546/165; 546/146

[58] Field of Search ..... 548/492, 533; 514/423

[56] References Cited

U.S. PATENT DOCUMENTS

| | | | |
|---|---|---|---|
| 4,374,829 | 2/1983 | Harris et al. | 424/177 |
| 4,402,969 | 9/1983 | Greenlee et al. | 424/724 |
| 4,432,971 | 2/1984 | Karanewsky et al. | 424/177 |
| 4,452,790 | 6/1984 | Karanewsky et al. | 424/200 |
| 4,470,973 | 9/1984 | Matarajan | 548/492 |
| 4,479,772 | 5/1984 | Karanewsky | 548/112 |
| 4,515,803 | 5/1985 | Henning et al. | 514/338 |
| 4,555,506 | 11/1985 | Karanewsky et al. | 514/91 |
| 4,568,489 | 2/1986 | Floyd | 548/533 X |

FOREIGN PATENT DOCUMENTS

| | | |
|---|---|---|
| 17203 | 4/1983 | Australia . |
| 18549 | 4/1980 | European Pat. Off. . |
| 61745 | 2/1982 | European Pat. Off. . |
| 61684 | 6/1982 | European Pat. Off. . |
| 0080822 | 6/1983 | European Pat. Off. . |
| 74070 | 7/1983 | European Pat. Off. . |

OTHER PUBLICATIONS

Tanabe, Abstract of Japanese Patent Application 5-51-51-555.

Kureha Chem. Ind., Abstract of Japanese Patent Application 5-8170-752A.

*Primary Examiner*—John F. Terapane
*Assistant Examiner*—Richard Treanor
*Attorney, Agent, or Firm*—Lawrence S. Levinson; Stephen B. Davis

[57] ABSTRACT

Compounds of the formula wherein X is various imino or amino acids or esters are disclosed. These compounds possess angiotensin converting enzyme inhibition activity and depending upon the definition of X also possess enkephalinase inhibition activity.

12 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SUBSTITUTED URIDO AMINO AND IMINO ACIDS AND ESTERS

BACKGROUND OF THE INVENTION

Yoneda et al. in European Patent Application No. 18,549 discloses angiotensin converting enzyme inhibitors having a carboxyalkylaminocarbonyl sidechain coupled to the N-atom of tetrahydroisoquinoline. Similarly, Tanabe in Japanese Patent Application No. J55151-555 discloses angiotensin converting enzyme inhibitors where the carboxyaminocarbonyl sidechain is coupled is L-proline. Yoneda et al. in European Patent Application No. 61,745 discloses angiotensin converting enzyme inhibitors having an alkyl or aralkyl substituted carboxyalkylaminocarbonyl sidechain coupled to the N-atom of tetrahydroisoquinoline and Kureha Chem. discloses such sidechains coupled to L-proline in Japanese Patent Application No. J5 8170-752-A.

Patchett et al. in European Patent Application No. 61,684 disclose that various substituted carboxyalkylaminocarbonyl amino and imino acids and esters possess angiotensin converting enzyme inhibition activity. Similarly, Henning et al. in European Patent Application No. 74,070 also disclose that various substituted carboxyalkylaminocarbonyl amino and imino acids and esters possess angiotensin converting enzyme inhibition activity.

Natarajan et al. in Australian Patent Application No. 17,203 disclose that various acylaminoalkanoylaminocarbonyl substituted amino and imino acids and esters possess angiotensin converting enzyme inhibition activity.

SUMMARY OF THE INVENTION

This invention is directed to new substituted ureido amino and imino acids and esters and pharmaceutically acceptable salts thereof of the formula

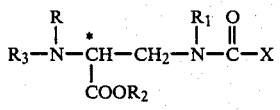

(I)

X is an amino or imino acid or ester of the formula

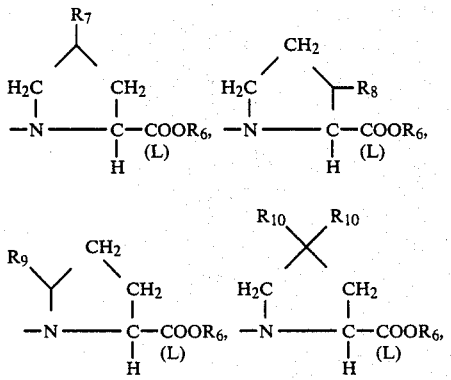

-continued

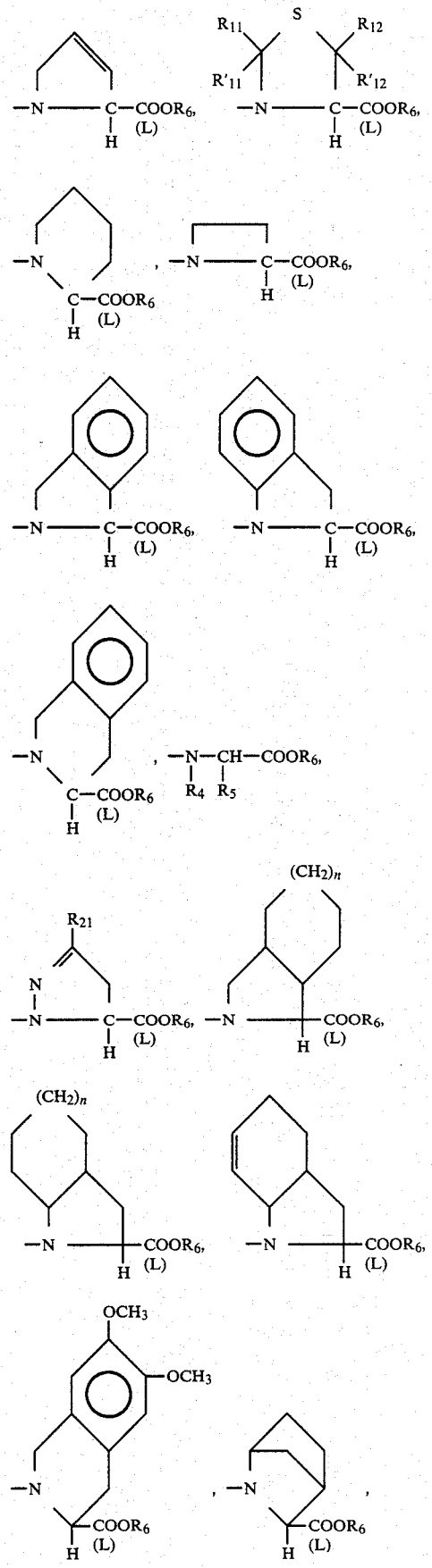

-continued
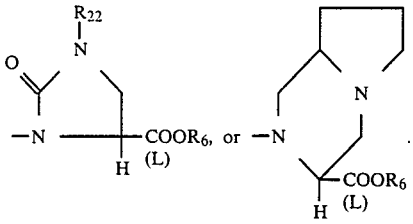
n is zero, one or two.
$R_{22}$ is lower alkyl of 1 to 4 carbons or
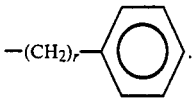
$R_7$ is hydrogen, lower alkyl, halogen, hydroxy,
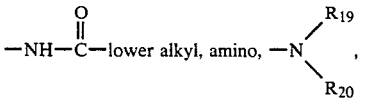
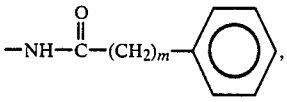
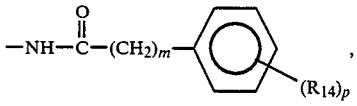
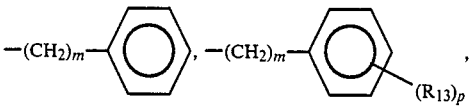
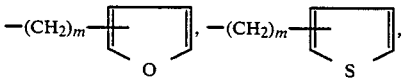
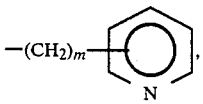
a 1- or 2-naphthyl of the formula
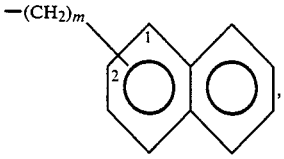
a substituted 1- or 2-naphthyl of the formula
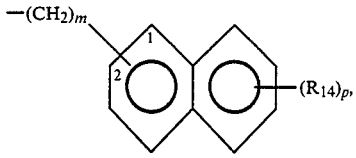
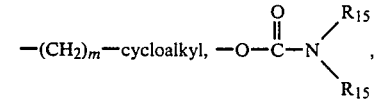
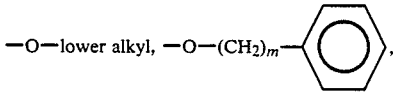
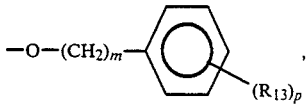
a 1- or 2-naphthyloxy of the formula
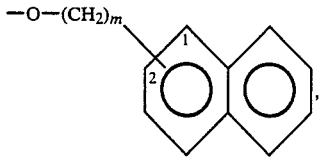
a 1- or 2-naphthyloxy of the formula
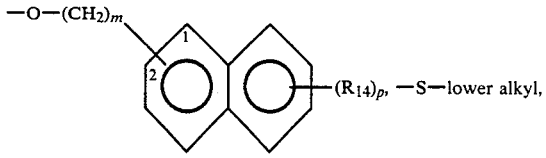
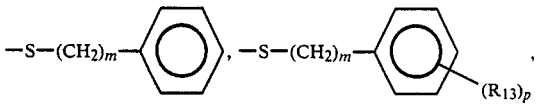
a 1- or 2-naphthylthio of the formula
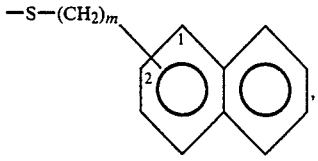
or a substituted 1- or 2-naphthylthio of the formula
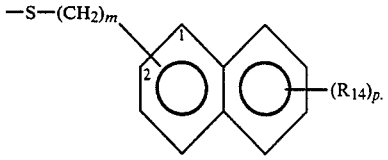
$R_8$ is halogen

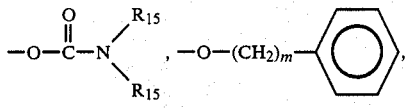

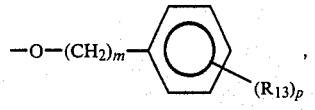

—O—lower alkyl, a 1— or 2-napthyloxy of the formula

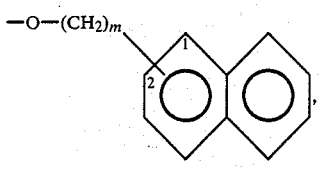

a substituted 1- or 2-naphthyloxy of the formula

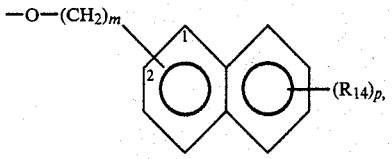

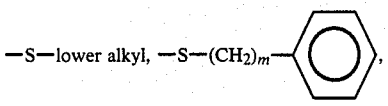

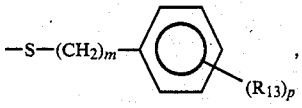

a 1- or 2-naphthylthio of the formula

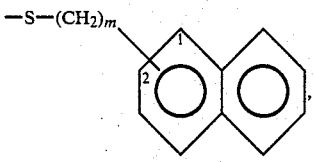

or a substituted 1- or 2-naphthylthio of the formula

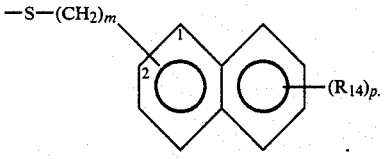

$R_9$ is Keto,

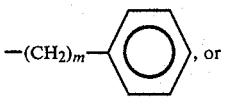

-continued

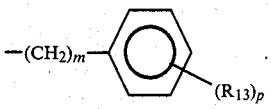

$R_{10}$ is halogen or —Y—$R_{16}$. $R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

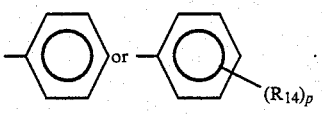

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one two, three, or four.

p is one, two or three provided that p is more than one only if $R_{13}$ or $R_{14}$ is methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

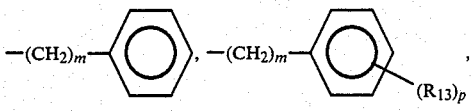

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl,

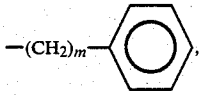

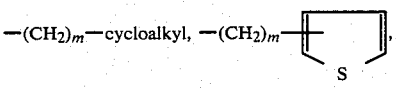

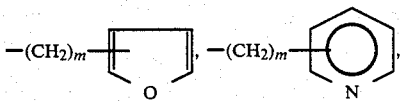

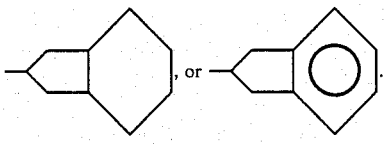

$R_5$ is hydrogen, lower alkyl,

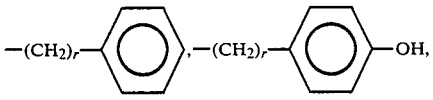

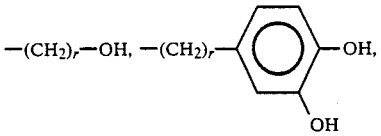

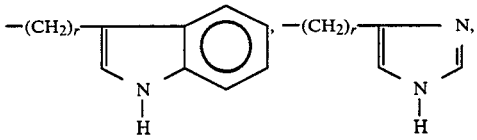

$-(CH_2)_r-NH_2$, $-(CH_2)_r-SH$, $-(CH_2)_r-S-$lower alkyl,

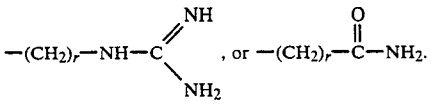

r is an integer from 1 to 4.

$R_{19}$ is lower alkyl, benzyl, or phenethyl.

$R_{20}$ is hydrogen, lower alkyl, benzyl or phenethyl.

$R_1$ is hydrogen, lower alkyl, halo substituted lower alkyl

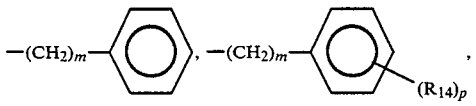

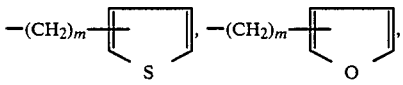

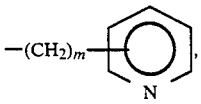

$-(CH_2)_m-$cycloalkyl, $-(CH_2)_2-NH_2$,

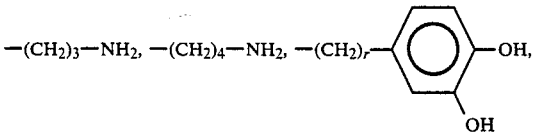

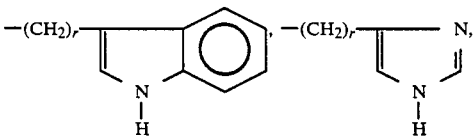

$-(CH_2)_r-SH$, $-(CH_2)_r-OH$, $-(CH_2)_r-S-$lower alkyl,

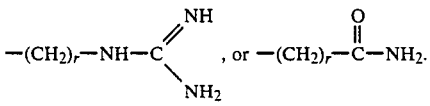

R is hydrogen, lower alkyl

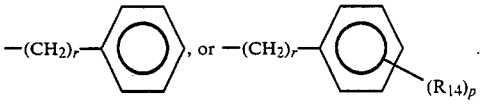

$R_3$ is hydrogen, lower alkyl

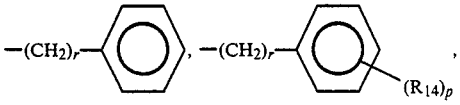

$-C(=O)-$lower alkyl, $-C(=O)-(CH_2)_m-$cycloalkyl,

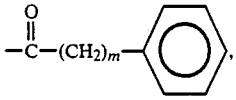

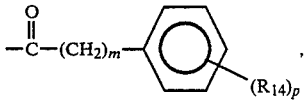

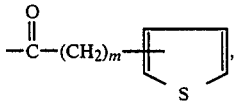

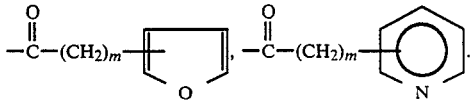

$R_2$ and $R_6$ are independently selected from hydrogen, lower alkyl, benzyl, benzhydryl,

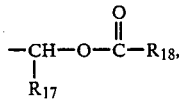

and salt forming ion.

$R_{17}$ is hydrogen, lower alkyl, cycloalkyl, or phenyl.

$R_{18}$ is hydrogen, lower alkyl, lower alkoxy, or phenyl.

$R_{21}$ is hydrogen, lower alkyl,

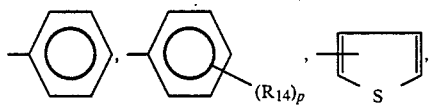

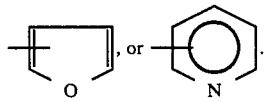

DETAILED DESCRIPTION OF THE INVENTION

This invention in its broadest aspects relates to the substituted ureido amino and imino acids and esters of formula I above, to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

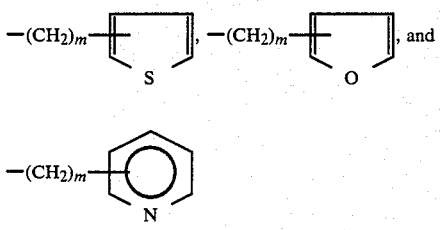

represent that the alkylene bridge is attached to an available carbon atom.

The compounds of formula I wherein at least one of $R_3$ and R is other than hydrogen can be prepared by various methods. For example a carboxylic acid ester compound of the formula

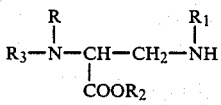

(II)

wherein $R_2$ is lower alkyl, benzyl or benzhydryl is coupled with the acid chloride of the formula

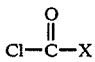

(III)

in the presence of N-methyl morphline wherein $R_6$ in the definition of X is an easily removable ester protecting group such as benzyl, benzhydryl or lower alkyl. The $R_2$ and $R_6$ ester groups can be removed by conventional procedures, i.e. hydrogenation when $R_2$ or $R_6$ is benzyl or benzhydryl, treatment with sodium or lithium hydroxide when $R_2$ or $R_6$ is an alkyl such as methyl or ethyl, or treatment with trifluoroacetic acid when $R_2$ or $R_6$ is t-butyl, to yield the products of formula I wherein $R_2$ and $R_6$ are hydrogen.

The intermediates of formula II wherein $R_3$ is an acyl group and R is hydrogen can be prepared as follows. An amino compound of the formula

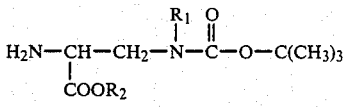

(IV)

is reacted with the particular acyl chloride in the presence of pyridine followed by treatment with trifluoroacetic acid to remove the t-butoxycarbonyl protecting group.

The intermediates of formula II wherein R and $R_3$ are lower alkyl, aralkyl, or heteroalkyl or $R_3$ is acyl can be prepared as follows. An amino compound of the formula

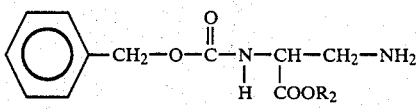

(V)

wherein $R_2$ is an ester group is treated with trifluoroacetic acid to yield the acetate

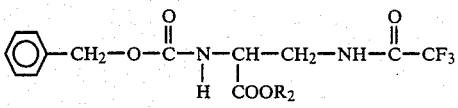

(V)

When $R_1$ is other than hydrogen, the acetate of formula VI is reacted with the alkylating agent of the formula $R_1$-halo (VII)

in the presence of base, such as sodium hydride, to give

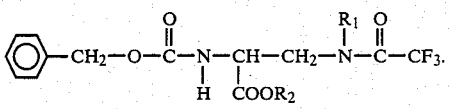

(VIII)

Hydrogenation in the presence of palladium on carbon catalyst gives the amine of the formula

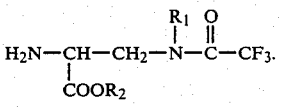

(IX)

The acetate of formula IX is then reacted with the aldehyde of the formula

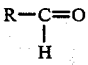

(X)

in ethanol under a hydrogen atmosphere in the presence of a Raney nickel catalyst to give

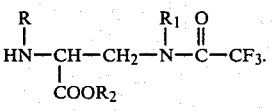

(XI)

The compound of formula XI can then be reacted with an aldehyde of the formula

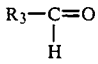

(XII)

under the same conditions described above or reacted with an acyl chloride in the presence of pyridine to give

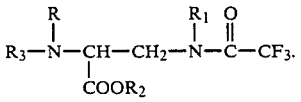

(XIII)

Treatment with sodium borohydride in ethanol removes the trifluoroacetate and gives the intermediate of formula II.

The intermediates of formula II wherein R is hydrogen and $R_3$ is acyl can also be prepared by treating an acyl azetidinone of the formula

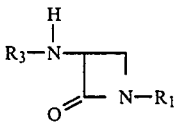

(XIV)

with sodium methoxide in methanol to give

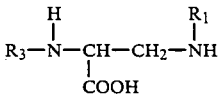

(XV)

which is then treated to introduce the $R_2$ ester group.

The compounds of formula I wherein R and $R_3$ both hydrogen can be prepared by reacting the amine of formula IX with N-carboethoxy phthalimide and potassium carbonate in aqueous dioxane to give (XVI)

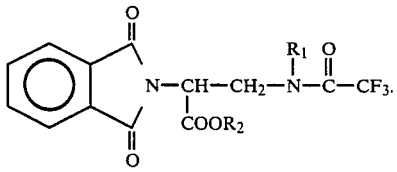

(XVI)

Treatment with sodium borohydride gives the intermediate of the formula

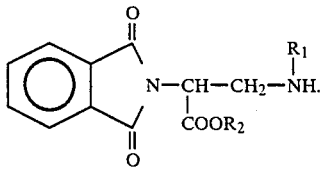

(XVII)

The intermediate of formula XVII is then coupled with the acid chloride of formula III to

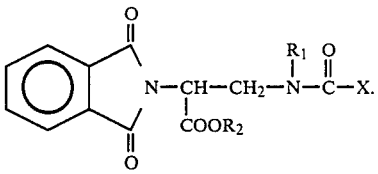

(XVIII)

Treatment with a slight excess of methyl hydrazine in benzene removes the phthalimido protecting group.

The acid chloride amino or imino acid ester of formula III is prepared by treating the corresponding amino or imino acid ester hydrochloride with phosgene in the presence of N-methyl morpholine.

In the above reactions if either $R_1$ or $R_5$ or both are

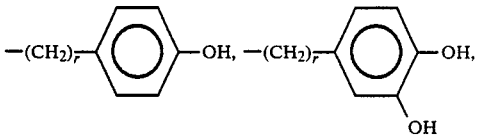

$-(CH_2)_r-NH_2$, $-(CH_2)_r-SH$, $-(CH_2)_r-OH$,

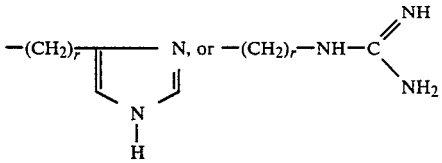

then the hydroxyl, amino, imidazolyl, mercaptan, or guanidinyl function should be protected during the reaction. Suitable protecting groups include benzoyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The ester products of formula I wherein $R_6$ is

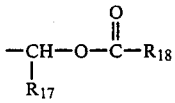

may be obtained by employing the imino or amino acid of formula III in the above reactions with the ester group already in place. Such ester reactants can be prepared by treating the imino or amino acid with an acid chloride such as

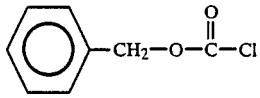

so as to protect the N-atom. The protected compound is then reacted in the presence of a base with a compound of the formula

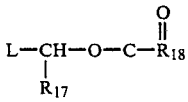

(XIX)

wherein L is a leaving group such as chlorine, bromine, tolylsulfonyl, etc., followed by removal of the N-protecting group such as by treatment with acid or hydrogenation.

The ester products of formula I wherein $R_6$ is

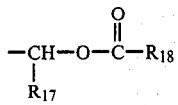

can also be obtained by treating the product of formula I wherein $R_6$ is hydrogen with a molar equivalent of the compound of formula XIX. The diester products wherein $R_2$ and $R_6$ are the same and are

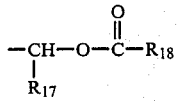

can be obtained by treating the product of formula I wherein $R_2$ and $R_6$ are both hydrogen or an alkali metal salt with two or more equivalents of the compound of formula XIX.

The ester products of formula I wherein $R_2$ is

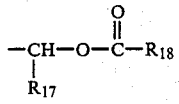

can be obtained by treating the product of formula I wherein $R_2$ is hydrogen or an alkali metal salt and $R_6$ is benzyl or benzhydryl with the compound of formula XIX in the presence of base. Removal of the $R_6$ ester group such as by hydrogenation yields the products of formula I wherein

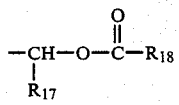

and $R_6$ is hydrogen.

The products of formula I wherein $R_7$ is amino may be obtained by reducing the corresponding products of formula I wherein $R_7$ is azido.

Preferred compounds of this invention with respect to the imino or amino acid or ester part of the structure of formula I are those wherein:

$R_4$ is hydrogen, cyclohexyl or phenyl.

$R_5$ is hydrogen, straight or branched chain lower alkyl of 1 to 4 carbons, $—CH_2OH$,

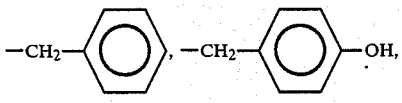

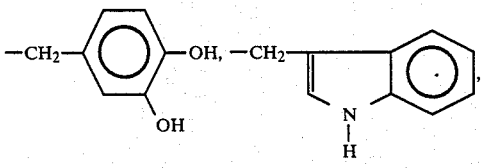

-continued

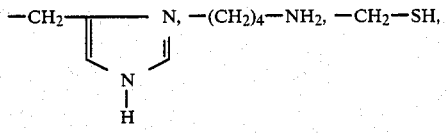

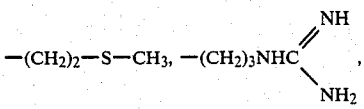

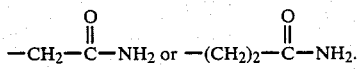

$R_6$ is hydrogen, straight or branched chain lower alkyl of 1 to 4 carbons, alkali metal salt ion or

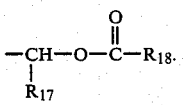

$R_{17}$ is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

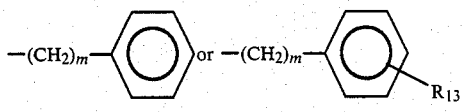

wherein m is zero, one or two and $R_{13}$ is methyl, methoxy, methylthio, chloro, bromo, fluoro, or hydroxy.

$R_7$ is

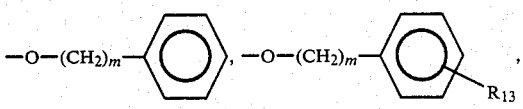

1-naphthyloxy, or 2-naphthyloxy wherein m is zero, one, or two and $R_{13}$ is methyl, methoxy, methylthio, chloro, bromo, fluoro, or hydroxy.

$R_7$ is -S-lower alkyl wherein lower alkyl is straight or branched chain of 1 to 4 carbons.

$R_7$ is

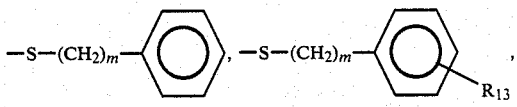

1-naphthylthio, or 2-naphthylthio wherein m is zero, one, or two and R is methyl, methoxy, methylthio, chloro, bromo, fluoro or hydroxy.

$R_8$ is —O—lower alkyl wherein lower alkyl is straight or branched chain of 1 to 4 carbons. $R_8$ is

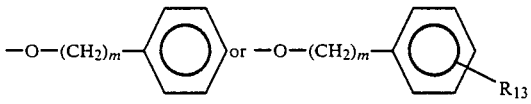

wherein m is zero, one, or two and $R_{13}$ is methyl, methoxy, methylthio, chloro, bromo, fluoro, or hydroxy.

$R_8$ is —S—lower alkyl wherein lower alkyl is straight or branched chain of 1 to 4 carbons.

$R_8$ is

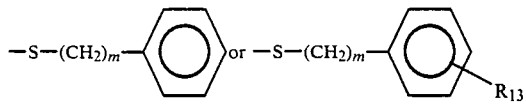

wherein m is zero, one or two and $R_{13}$ is methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or oranched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R'_{11}$, $R_{12}$ and $R'_{12}$ are all hydrogen, or $R_{11}$ is phenyl, 2-hydroxyphenyl, or 4-hydroxyphenyl and $R'_{11}$, $R_{12}$ and $R'_{12}$ are hydrogen. $R_{21}$ is phenyl.

Most preferred compounds of this invention with respect to the imino or amino acid or ester part of the structure of formula I are those wherein:

X is

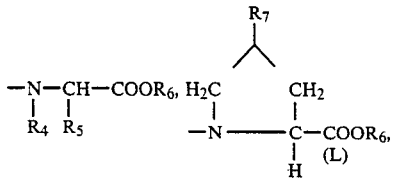

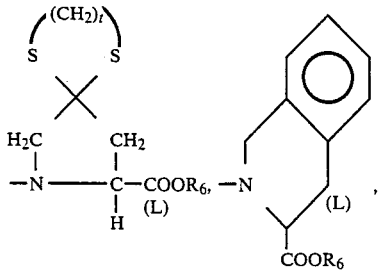

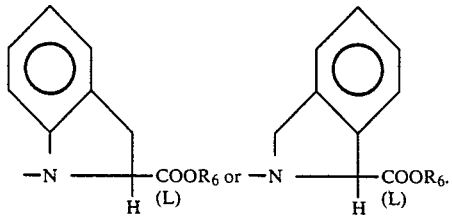

$R_6$ is hydrogen or an alkali metal salt ion.

$R_4$ is cyclohexyl or phenyl and $R_5$ is hydrogen.

$R_4$ is hydrogen and $R_5$ is methyl,

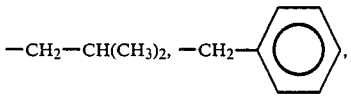

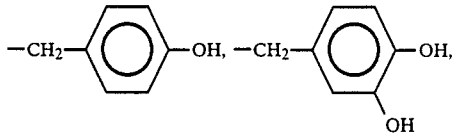

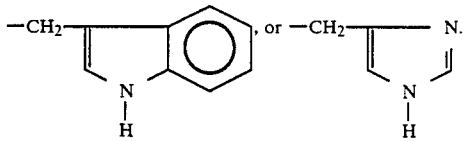

$R_7$ is hydrogen, cyclohexyl, lower alkoxy of 1 to 4 carbons,

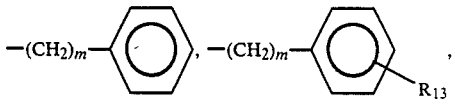

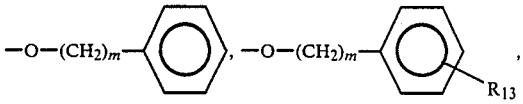

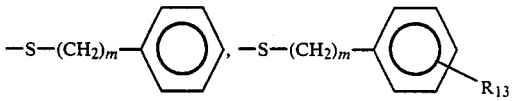

wherein m is zero, one, or two and $R_{13}$ is methyl, methoxy, methylthio, Cl, Br, F, or hydroxy, especially preferred wherein $R_7$ is hydrogen.

t is two or three, especially where t is two.

Preferred compounds of this invention with respect to the carboxyl containing sidechain portion of the structure of formula I are those wherein:

R is hydrogen.

$R_1$ is straight or branched chain lower alkyl of 1 to 4 carbons, benzyl,

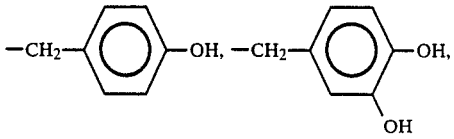

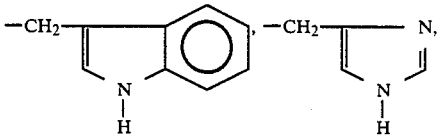

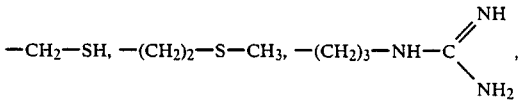

$-(CH_2)_2-NH_2$, $-(CH_2)_3-NH_2$, $-(CH_2)_4-NH_2$,

-continued

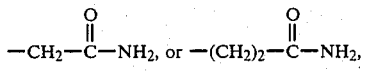

especially ethyl.

$R_2$ is hydrogen, straight or branched chain lower alkyl of 1 to 4 carbons, alkali metal salt ion, or

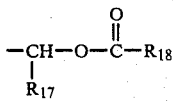

wherein $R_{17}$ is hydrogen, straight or branched chain lower alkyl of 1 to 4 carbons, or cyclohexyl and $R_{18}$ is straight or branched chain lower alkyl of 1 to 4 carbons or phenyl, especially wherein $R_2$ is hydrogen or alkali metal salt.

$R_3$ is

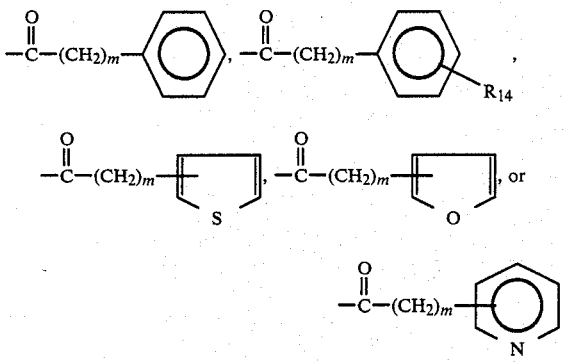

wherein m is zero, one or two and $R_{14}$ is methyl, methoxy, methylthio, chloro, bromo, fluoro, or hydroxy, especially wherein $R_3$ is

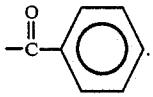

The compounds of formula I wherein $R_2$ or $R_6$ or both are hydrogen form salts with a variety of inorganic or organic bases. The non-toxic, pharmaceutically acceptable salts are preferred, although other salts are also useful in isolation or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Also, the compounds of formula I containing a free amino function form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

The compounds of formula I contain an asymmetric center in the carboxyl sidechain represented by *. Thus, the compounds of formula I can exist in diasteroisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted also give rise to cis-trans isomerism. The configuration of the final product will depend upon the configuration of the $R_7$, $R_8$ and $R_9$ substituent in the starting material of formula III.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinagen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinagen →(renin)→angiotensin I→(ACE)→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 25 mg. per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in a effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

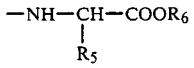

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 25 mg. per kilogram per day, produces the desired analgesic activity. The composition is preferably administered orally but parenteral routes such as subcutaneous can also be employed.

The following examples are illustrative of the invention. Temperatures are given in degrees centigrade. HP-20 refers to a neutral polystyrene resin commercially available from Mitsubishi.

EXAMPLE 1

1-[[[2-(Benzoylamino)-2-carboxyethyl]ethylamino]carbonyl]-L-proline, disodium salt (isomer A and isomer B)

(a) (S)-(1-Ethyl-2-oxo-3-azetidinyl)carbamic acid, phenylmethyl ester 1.69M n-Butyllithium (14.1 ml., 23.8 mmole) is added to a solution of hexamethyldisilazane (5.3 ml., 24.9 mmole) in ethyl ether (30 ml.) under an argon atmosphere at −78°. After stirring at −78° for one hour, a solution of (S)-(2-oxo-3-azetidinyl)carbamic acid, phenylmethyl ester (5.0 g., 22.7 mmole) in tetrahydrofuran (150 ml.) is added over a period of 30 minutes. After stirring an additional hour, 1M triethyloxonium tetrafluoroborate (27 ml., 27.2 mmole) in methylene chloride solution is added and the mixture is allowed to gradually reach room temperature overnight. All volatiles are then removed in vacuo. Ethyl acetate/water work-up on the residue followed by flash chromatography (1:1 ethyl acetate:toluene) yields 2.53 g. of (S)-(1-ethyl-2-oxo-3-azetidinyl)carbamic acid, phenylmethyl ester as a light yellow viscous oil.

(b) (S)-3-Amino-1-ethyl-2-azetidinone, 4-methylbenzenesulfonic acid salt

A magnetically stirred mixture of (S)-(1-ethyl-2-oxo-3-azetidinyl)carbamic acid, phenylmethyl ester (2.5 g., 10.2 mmole), 0.5 g. of 10% palladium on carbon catalyst, and 50 ml. of methanol is allowed to stir under hydrogen for 4 hours. The mixture is then filtered (Celite) and 4-methylbenzenesulfonic acid (2.09 g., 11.0 mmole) is added. The solution is then concentrated and the the mixture is rotary evaporated to give 2.53 g. of (S)-3-amino-1-ethyl-2-azetidinone, 4-methylbenzenesulfonic acid salt as a light yellow oil.

(c) (S)-3-(Benzoylamino)-1-ethyl-2-azetidinone

N,N-Dimethylamino pyridine (2.70 g., 22.1 mmole) is added to a magnetically stirred solution of (S)-3-amino-1-ethyl-2-azetidinone-4-methylbenzenesulfonic acid salt (2.53 g., 8.84 mmole) and benzoyl chloride (1.54 ml., 13.3 mmole) in methylene chloride (20 ml.) under argon. After stirring overnight, the solution is washed with 10% aqueous hydrochloric acid, 5% aqueous sodium bicarbonate, brine, dried ($MgSO_4$), filtered, and rotary evaporated. Flash chromatography (2:1 ethyl acetate:toluene) gives 1.4 g. of (S)-3-(benzoylamino)-1-ethyl-2-azetidinone as a light yellow oil.

(d) 2-(Benzoylamino)-3-(ethylamino)propanoic acid

Sodium methoxide (0.17 g., 3.2 mmole) is added to a magnetically stirred solution of (S)-3-(benzoylamino)-1-ethyl-azetidinone (0.35 g., 1.6 mmole) in methanol (5 ml.) under argon. After stirring at room temperature for five hours, the solution is poured into 10% aqueous hydrochloric acid and the aqueous layer is washed with ethyl acetate. The aqueous layer is then rotary evaporated and the residue run through an AG-50W-X2 column eluting with 1N $NH_4OH$. The effluent, after standing 2 days, is lyophilized to give 0.32 g. 2-(benzoylamino)-3-(ethylamino)propanoic acid as a white solid.

(e) 2-(Benzoylamino)-3-(ethylamino)propanoic acid, methyl ester, hydrochloride (1:1)

2-(Benzoylamino)-3-(ethylamino)propanoic acid (0.32 g., 1.35 mmole) is added to a magnetically stirred solution of thionyl chloride (0.4 ml.) in methanol (1.5 ml.) at 0° under argon. After stirring at room temperature overnight, all volatiles are removed in vacuo to give 0.37 g. of 2-(benzoylamino)-3-(ethylamino)-propanoic acid, methyl ester, hydrochloride (1:1) as an off-white solid.

(f) 1-[[[2-(Benzoylamino)-3-methoxy-3-oxopropyl]ethylamino]carbonyl]-L-proline, phenylmethyl ester A suspension of 2-(benzoylamino)-3-(ethylamino)-propanoic acid, methyl ester, hydrochloride (1:1) (0.15 g., 0.52 mmole) and N-methylmorpholine (0.17 ml., 1.56 mmole) in methylene chloride (5 ml.) is added to a stirred solution of 0.62 ml. of phosgene solution (0.78 mmole of a 1.25 M solution in benzene) in methylene chloride (1 ml.) at −30° under argon. After stirring for one hour at −30° one hour at room temperature, all volatiles are removed in vacuo. Methylene chloride is then added and the mixture is concentrated once again. The residue is taken up in methylene chloride (5 ml.) and L-proline, phenylmethyl ester, hydrochloride (1:1) (0.15 g., 0.62 mmole) followed by N-methyl morpholine (0.14 ml., 1.25 mmole) in methylene chloride (1 ml.) are added. After stirring overnight, the mixture is partitioned between ethyl acetate and water. The ethyl acetate layer is washed with 10% hydrochloric acid, 5% sodium bicarbonate, and brine, dried ($MgSO_4$), filtered, and rotary evaporated leaving a yellow oil. Flash chromatography (3:1 hexane:acetone) gives 0.26 g. of 1[[[2-(benzoylamino)-3-methoxy-3-oxopropyl]ethylamino]-carbonyl]-L-proline, phenylmethyl ester as a colorless oil.

(g) 1-[[[2-(Benzoylamino)-3-methoxy-3-oxopropyl]ethylamino]carbonyl]-L-proline A magnetically stirred mixture of the phenylmethyl ester product from part (f) (0.26 g., 0.50 mmole), 10% palladium on carbon catalyst (30 mg.) and methanol (10 ml.) is allowed to stir under hydrogen for one hour. The mixture is then filtered (Celite) and the filtrate rotary evaporated to give 0.20 g. of 1-[[[2-(benzoylamino)-3-methoxy-3-oxopropyl]ethylamino]carbonyl]-L-proline as a colorless glass.

(h)

1-[[[2-(Benzoylamino)-2-carboxyethyl]ethylamino]carbonyl ]-L-proline, disodium salt (isomer A and isomer B).

Sufficient methanol is added to a magnetically stirred solution of the product from part (g) (0.20 g., 0.50 mmole), tetrahydrofuran (5 ml.), and 0.5 N sodium hydroxide (5 ml.) to effect solution. After stirring overnight, the solution is rotary evaporated and the residue is applied to an HP-20 column eluting with water→methanol gradient. The elution profile (silica gel, 4:1:1 n-butanol:acetic acid:water) shows the separation of two compounds with identical $R_f$ values (0.56). The first compound to elute after lyophilization gives 0.11 g. of 1-[[[2-(benzoylamino)-2-carboxyethyl]ethylamino]carbonyl]-L-proline, disodium salt (isomer A) as a white solid; m.p. greater than 250°.

Anal. calc'd. for $C_{18}H_{21}N_3O_6Na_2$.2.17M $H_2O$ and 0.70M NaOH : C, 44.26; H, 5.37; N, 8.60; Na, 12.71. Found: C, 44.26; H, 5.15; N, 8.23; Na, 12.33.

The second compound to elute after lyophilization gives 0.10 g. of 1-[[[2-(benzoylamino)-2-carboxyethyl]ethylamino]carbonyl]-L-proline, disodium salt (isomer B) as a white solid; m.p. greater than 250°.

Anal. calc'd. for $C_{18}H_{21}N_3O_6Na_2$.2.72M $H_2O$: C, 45.96; H, 5.67; N, 8.94. Found: C, 45.96; H, 5.35; N, 9.06.

EXAMPLE 2

[1(R),3S]-1[[[2-(Benzoylamino)-2-carboxyethyl]ethylamino]carbonyl]-2,3-dihydro-1H-indole-2-carboxylic acid, dilithium salt (a)

(R)-4-Amino-2-[[(benzyloxy)carbonyl]amino]-4-oxobutanoic acid

A solution of benzyl chloroformate (58.32 ml., 0.41 mole) in tetrahydrofuran (50 ml.) is added dropwise to a solution of D(-)asparagine hydrate (50 g., 0.33 mole) dissolved in 1 l. of saturated sodium bicarbonate. The solution is allowed to stir at room temperature for 6 hours and then extracted with ethyl acetate (3×200 ml.). The aqueous layer is concentrated in vacuo to remove traces of ethyl acetate, then acidified to pH of 3. A white precipitate is collected and subsequently washed with water and then dried over phosphorus pentoxide to give 74 g. of (R)-4-amino-2-[[(benzyloxy)carbonyl]amino]-4-oxobutanoic acid, m.p. 206°-210°.

(b)

(R)-3-Amino-2-[[(benzyloxy)carbonyl]amino]-propanoic acid

[Bis(trifluoroacetoxy)iodo]benzene (6.45 g., 15.0 mmole) is dissolved in water-dimethylformamide 1:1 (80 ml.) and (R)-4-amino-2-[[(benzyloxy)carbonyl]amino]-4-oxobutanoic acid (2.4 g., 9.0 mmole) is added over a 10 minute period. The reaction is allowed to stir at room temperature for 30 minutes, until dissolution occurs. Pyridine (1.62 ml., 20 mmole) is added dropwise over a 5 minute period. The reaction is allowed to stir for 3 hours then stripped of solvent to yield a yellow precipitate. This semi-solid is triturated with a combination of isopropanol:ethyl ether. The precipitate is filtered and dried over phosphorus pentoxide to yield 1.35 g. of (R)-3-amino-2-[[(benzoyloxy)carbonyl]amino]-propanoic acid as a white solid.

(c)

(R)-3-(Acetylamino)-2-[[(benzyloxy)carbonyl]amino]-propanoic acid

A solution of acetic anhydride (0.66 ml., 7.0mmole) in tetrahydrofuran (5 ml.) is added to a solution of (R)-3-amino-2-[[(benzyloxy)carbonyl]amino]propanoic acid (1.0 g., 4.3 mmole) dissolved in 40 ml. of saturated sodium bicarbonate and 10 ml. of tetrahydrofuran. The reaction is allowed to stir overnight and the aqueous layer is extracted with ethyl acetate (2×50 ml.). The aqueous layer is acidified to pH of 2 and extracted with ethyl acetate (4×70 ml.). The combined extracts are washed with saturated sodium chloride and dried over sodium sulfate. The solvent is removed in vacuo to yield 1.08 g. of (R)-3-(acetylamino)-2-[[(benzyloxy)carbonyl]amino]propanoic acid as an amorphous solid.

(d)

(R)-3-(Acetylamino)-2-[[(benzyloxy)carbonyl]amino]-propanoic acid, ethyl ester 1,8-Diazabicyclo[5.4.0]undec-7-ene (0.45 ml., 3.0 mmole) and ethyl iodide (0.3 ml., 3.75 mmole) are added to a solution of (R)-3-(acetylamino)-2-[[(benzyloxy)carbonyl]amino]propanoic acid (0.7 g., 2.5 mmole) in acetonitrile (15 ml.). The reaction is allowed to stir overnight then concentrated in vacuo. The residue is dissolved in methylene chloride, washed with 2N hydrochloric acid (2×50 ml.), sodium bicarbonate (2×50 ml.), and brine, and then dried over sodium sulfate. The solvent is removed in vacuo and the resulting oil is chromatographed on silica gel eluting with ethyl acetate to yield 0.6 g. of (R)-3-(acetylamino-2-[[(benzyloxy)carbonyl]amino]propanoic acid, ethyl ester as a clear oil.

(e)

(R)-2-[[(Benzyloxy)carbonyl]amino]-3-(ethylamino)-propanoic acid, ethyl ester

A 10 M solution of boranemethylsulfide (3.3 ml., 33.0 mmole) is added dropwise to a solution of (R)-3-(acetylamino)-2-[[(benzyloxy)carbonyl]amino]-propanoic acid, ethyl ester (7.0 g., 22.7 mmole) in dry tetrahydrofuran (120 ml.) at 0°. The solution is stirred at room temperature for one hour and refluxed for 4 hours. After cooling to room temperature, 10 ml. of 10% hydrochloric acid is added dropwise followed by 15 ml. of 1N sodium hydroxide until the solution is at pH 9.5. The reaction mixture is then diluted with an equal volume of ethyl acetate. The aqueous layer is separated and reextracted with ethyl acetate (4×50 ml.). The combined organic layers are extracted with saturated sodium chloride and dried over sodium sulfate. The solvent is removed in vacuo to yield 5.5 g. of a yellowish oil. This oil is chromatographed on silica gel and eluted with (7:3) hexane:ethyl acetate. The product containing fractions are combined to give 3.3 g. of (R)-2-[[(benzyloxy)carbonyl]amino]-3-(ethylamino)-propanoic acid, ethyl ester as a clear oil.

$[\alpha]_D = +12.4$ (c=1.0, ethanol).

(f)

(R)-2-[[(Benzyloxy)carbonyl]amino]-3-[[(1,1-dimethylethoxy)carbonyl]ethylamino]propanoic acid, ethyl ester 1,1-Dimethylethoxy)carbonyl]carbonate (2.14 g., 9.82 mmole) in t-butanol (5 ml.) is added in one batch to a solution of (R)-2-[[(benzyloxy)carbonyl]amino]-3-(ethylamino)propanoic acid, ethyl ester (2.3 g., 7.82 mmole) in saturated sodium bicarbonate (50 ml.). The reaction is allowed to stir overnight. The mixture is then concentrated in vacuo and then extracted with ethyl acetate (4×50 ml.). The combined extracts are extracted with saturated sodium chloride and dried over sodium sulfate. The solvent is removed in vacuo, and the resulting oil is chromatographed on silica gel eluting with (1:1 ethyl acetate:hexane). The desired fractions are concentrated in vacuo to give 3.1 g. of (R)-2-[[(benzyloxy)carbonyl]amino]-3-[[(1,1-dimethylethoxy)carbonyl]ethylamino]propanoic acid, ethyl ester as a clear oil. $[\alpha]_D = +19.4$ (c=1.0, ethanol).

(g)

(R)-2-Amino-3-[[(1,1-dimethylethoxy)carbonyl]ethylamino]propanoic acid, ethyl ester A mixture of (R)-2-[[(benzyloxy)carbonyl]amino]-3-[[(1,1-dimethylethoxy)carbonyl]ethylamino ]propanoic acid, ethyl ester (2.3 g., 5.91 mmole) and 0.25 g. of 10% palladium on carbon catalyst in 50 ml. of absolute ethanol is stirred overnight under hydrogen atmosphere. The catalyst is filtered off and the ethanol solution is concentrated in vacuo to yield 1.55 g. of (R)-2-amino-3-[[(1,1-dimethylethoxy)carbonyl]ethylamino]propanoic acid, ethyl ester as a clear oil. $[\alpha]_D = -15.9°$ (c=1.0, ethanol).

(h)

(R)-2-Benzoylamino)-3-[[(1,1-dimethylethoxy)carbonyl]ethylamino]propanoic acid, ethyl ester Benzoyl chloride (0.698 ml., 6.0 mmole) is added dropwise to a solution of (R)-2-amino-3-[[(1,1-dimethylethoxy)carbonyl]ethylamino]propanoic acid, ethyl ester (1.55 g., 5.96mmole) and pyridine (0.97 ml., 12 mmole) in 25 ml. of methylene chloride. The reaction is allowed to stir at room temperature for 4 hours and then quenched with 5% potassium bisulfate. The organic layer is extracted with 5% potassium bisulfate (2×50 ml.), saturated sodium bicarbonate, and brine, and then dried over sodium sulfate. The solvent is removed in vacuo to yield 1.8 g. of a crude oil. This residue is chromatographed on silica gel and eluted with hexane then ethyl acetate to yield 1.4 g. of (R)-2-(benzoylamino)-3-[[(1,1-dimethylethoxy)carbonyl]ethylamino]propanoic acid, ethyl ester. $[\alpha]_D = +18.2°$ (c=1.0, ethanol).

(i) (R)-2-(Benzoylamino)-3-(ethylamino)propanoic acid, ethyl ester

A solution of (R)-2-(benzoylamino)-3-[[(1,1dimethylethoxy)carbonyl]ethylamino]propanoic acid, ethyl ester (1.1 g., 3.0 mmole) in trifluoroacetic acid is allowed to stir at room temperature for 2 hours. The solvent is then removed in vacuo, and the residue is dissolved in ethyl acetate and extracted with sodium bicarbonate. The aqueous sodium bicarbonate layer is back extracted with ethyl acetate (2×50 ml.). The combined extracts are washed with saturated sodium chloride and dried over sodium sulfate. The solvent is removed in vacuo and the residue is chromatographed on silica gel eluting with (1:1) ethyl acetate:hexane. The desired fractions are collected and stripped of solvent to yield 0.55 g. of (R)-2-(benzoylamino)-3(ethylamino)-propanoic acid, ethyl ester as a clear oil.

(j)

[1(R),3S]-1-[[2-(Benzoylamino)-2-carboxyethyl]ethylamino]carbonyl]-2,3-dihydro-1H-indole-2-carboxylic acid, diethyl ester A solution of 2-indolinecarboxylic acid, ethyl ester, hydrochloride (1:1) (0.1 g., 0.44 mmole) and N-methylmorpholine (0.1 ml., 0.99 mmole) in dry methylene chloride (5 ml.) is added rapidly to a solution of 12.5% phosgene in benzene (0.704 ml., 0.88 mmole) in dry methylene chloride (3 ml.) at −30°. The reaction is allowed to stir at −30° under argon for 30 minutes and at room for 30 minutes. The reaction mixture is stripped of solvent and chased with 5 ml. of methylene chloride. The residue is dissolved in methylene chloride (5 ml.) and (R)-2-(benzoylamino)-3-(ethylamino)propanoic acid, ethyl ester (0.121 g., 0.46 mmole) is added followed by N-methyl morpholine (0.1 ml., 0.99 mmole) and dimethylamino pyridine (0.10 g., 0.88 mmole). The reaction is allowed to stir at room temperature overnight and then diluted with methylene chloride. The organic layer is extracted with 2N hydrochloric acid (2×30 ml.), saturated sodium bicarbonate, brine, and dried over sodium sulfate. The solvent is removed in vacuo and the resulting oil is chromatographed on silica gel eluting with (4:1) ethyl acetate:hexane. The desired fractions are collected and stripped to yield 0.2 g. of [1(R),3S]-1-[[2-[(benzoylamino)-2-carboxyethyl]ethylamino]carbonyl]-2,3-dihydro-1H-indole-2-carboxylic acid, diethyl as a clear oil.

(k)

[1(R),3S]-1-[[2-[(Benzoylamino)-2-carboxyethyl]ethylamino]carbonyl]-2,3-dihydro-1H-indole-2-carboxylic acid, dilithium salt A mixture of the diethyl ester product from part (j) (200 mg., 0.42 mmole) in 1N sodium hydroxide (25 ml.) and tetrahydrofuran (5 ml.) is allowed to stir at room temperature for 4 hours. The reaction mixture is then extracted with ethyl acetate (2×20 ml.). The aqueous layer is acidified to pH of 2 and extracted with ethyl acetate (6×30 ml.). The combined extracts are dried over sodium sulfate and stripped of solvent to yield 180 mg. of an oil. The oil is dissolved in 1M lithium hydroxide (0.82 ml., 0.82 mmole) and chromatographed on an HP-20 column. The product is eluted with water and the desired fractions are lyophilized to give 88.3 mg. of [1(R),3S]-1-[[2-[(benzoylamino)-2-carboxyethyl]ethylamino]carbonyl]-2,3-dihydro-1H-indole-2-carboxylic acid, dilithium salt as a white solid; m.p. 240° (decomposes). TLC (silica gel, methylene chloride:methanol:$NH_4OH$; 85:15:1 $R_f$=0.25.

Anal. calc'd. for $C_{22}H_{21}N_3O_6$.2Li.2M $H_2O$: C, 55.71; H, 5.53; N, 8.86. Found: C, 55.65; H, 5.12; N, 8.86.

EXAMPLES 3 to 41

Following the procedures of Examples 1 and 2, the carboxylic acid ester shown in Col. I is coupled with the imino or amino acid ester shown in Col. II in the presence of phosgene to yield the compound shown in Col. III. Removal of the $R_2$ and $R_6$ ester groups yields the corresponding diacid product which can then be converted to a disalt. In the case of Examples 39 to 41 only the $R_2$ ester group would be removed.

Col. I
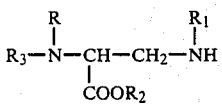
Col. II
-continued
HX
Col. III
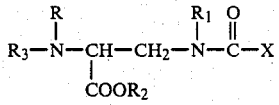

| Example | $R_3$ | R | $R_2$ | $R_1$ | X |
|---|---|---|---|---|---|
| 3 | 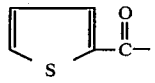 | —H | $-C_2H_5$ | $-C_2H_5$ | 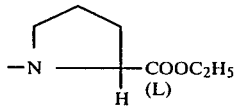 |
| 4 | 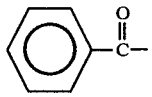 | —H | $-C_2H_5$ | 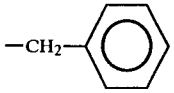 | 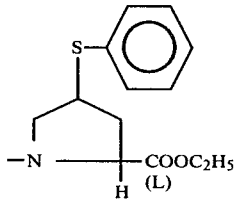 |
| 5 | 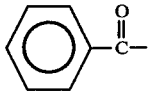 | —H | $-C_2H_5$ | 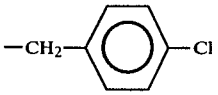 | 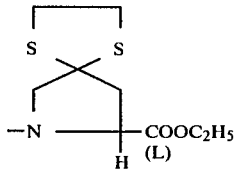 |
| 6 | 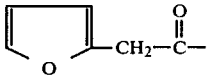 | $-CH_3$ | $-C_2H_5$ | $-C_2H_5$ | 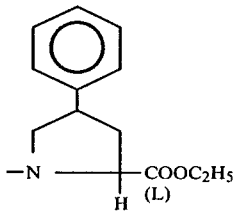 |
| 7 | 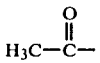 | —H | $-C_2H_5$ | —H | 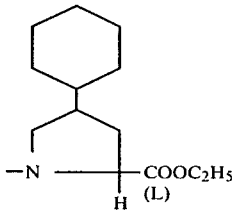 |

-continued
| Example | $R_3$ | R | $R_2$ | $R_1$ | X |
|---|---|---|---|---|---|
| 8 | 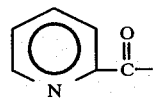 | —H | $-C_2H_5$ | $-C_2H_5$ | 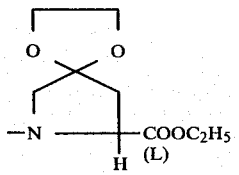 |
| 9 | 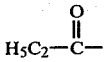 | —H | $-C_2H_5$ | 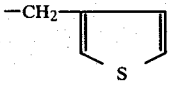 | 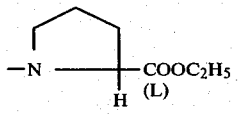 |
| 10 | 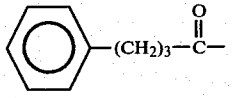 | —H | $-C_2H_5$ | $-CH_2CCl_3$ | 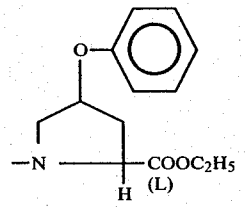 |
| 11 | $H_3C-$ | $-CH_3$ | $-C_2H_5$ | $-C_2H_5$ | 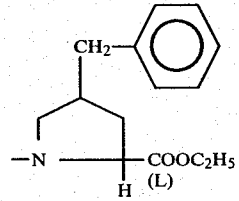 |
| 12 | $H_5C_2-$ | —H | $-C_2H_5$ | $-C_2H_5$ | 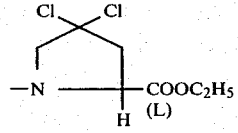 |

-continued
| Example | $R_3$ | R | $R_2$ | $R_1$ | X |
|---|---|---|---|---|---|
| 13 | 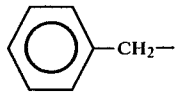 | —H | $-C_2H_5$ | $-C_2H_5$ | 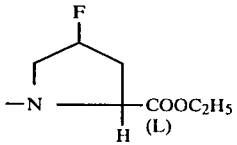 |
| 14 | 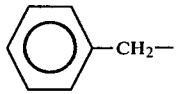 | $-CH_3$ | $-C_2H_5$ | $-C_2H_5$ | 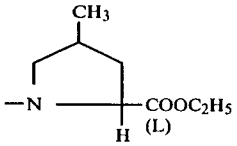 |
| 15 | 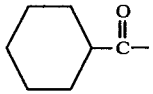 | —H | $-C_2H_5$ | —H | 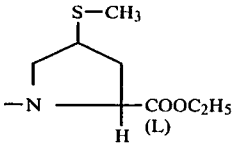 |
| 16 | 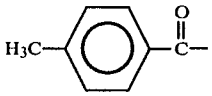 | —H | $-C_2H_5$ | $-C_2H_5$ | 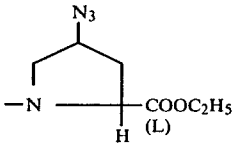 |
| 17 | 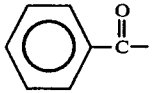 | —H | $-C_2H_5$ | 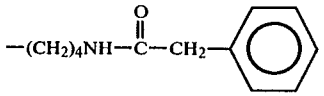 | 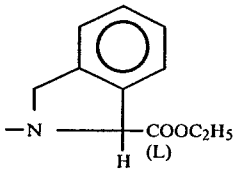 |
| 18 | 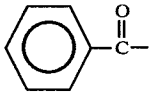 | —H | $-C_2H_5$ | 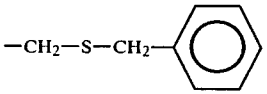 | 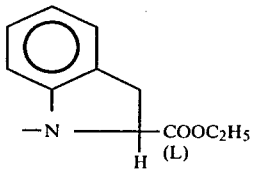 |

-continued
| Example | $R_3$ | R | $R_2$ | $R_1$ | X |
|---|---|---|---|---|---|
| 19 | 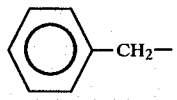 | —H | $-C_2H_5$ | 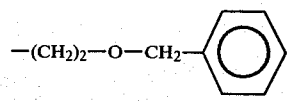 | 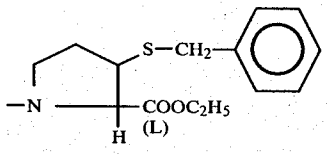 |
| 20 | 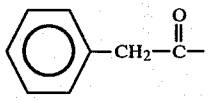 | —H | $-C_2H_5$ | $-C_3H_7$ | 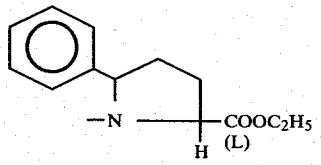 |
| 21 | 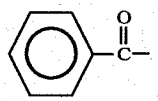 | —H | $-C_2H_5$ | 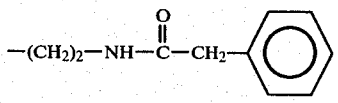 | 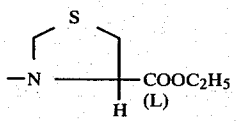 |
| 22 | 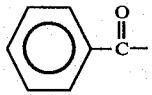 | —H | $-C_2H_5$ | $-C_2H_5$ | 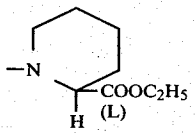 |
| 23 | 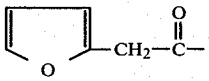 | —H | $-C_2H_5$ | $-CH_3$ | 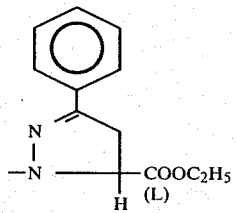 |

-continued
| Example | $R_3$ | R | $R_2$ | $R_1$ | X |
|---|---|---|---|---|---|
| 24 | 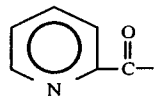 | —H | $-C_2H_5$ | $-C_2H_5$ | 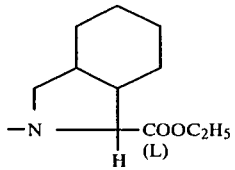 |
| 25 | 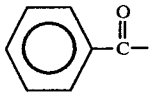 | —H | $-C_2H_5$ | $-C_2H_5$ | 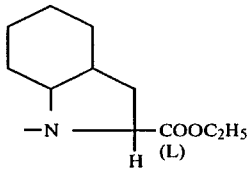 |
| 26 | 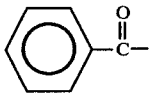 | —H | $-C_2H_5$ | $-C_2H_5$ | 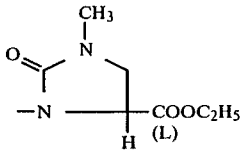 |
| 27 | 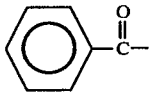 | —H | $-C_2H_5$ | $-C_2H_5$ | 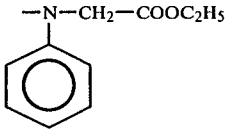 |
| 28 | 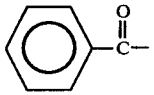 | —H | $-C_2H_5$ | $-C_2H_5$ | 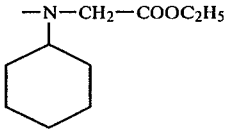 |
| 29 | 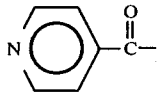 | —H | $-C_2H_5$ | 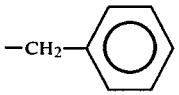 | 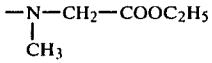 |

-continued
| Example | $R_3$ | R | $R_2$ | $R_1$ | X |
|---|---|---|---|---|---|
| 30 | 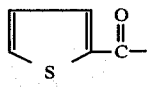 | —H | $-C_2H_5$ | $-C_2H_5$ | 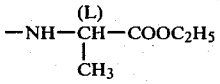 |
| 31 | 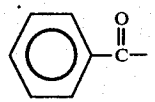 | —H | $-C_2H_5$ | $-C_2H_5$ | 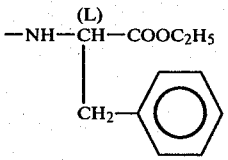 |
| 32 | $H_5C_2-$ | $-C_2H_5$ | $-C_2H_5$ | $-C_2H_5$ | 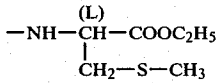 |
| 33 | 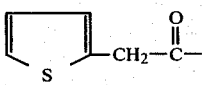 | —H | $-C_2H_5$ | $-C_2H_5$ | 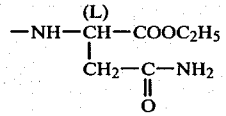 |
| 34 | 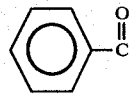 | —H | $-C_2H_5$ | $-C_2H_5$ | 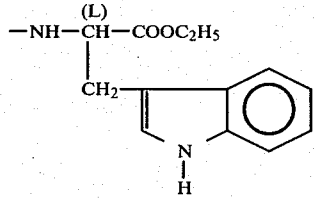 |
| 35 | 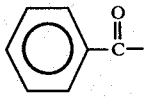 | —H | $-C_2H_5$ | $-C_2H_5$ | 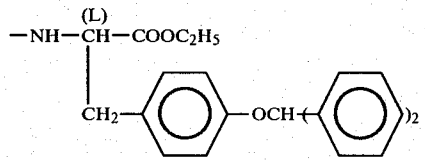 |

-continued
| Example | $R_3$ | R | $R_2$ | $R_1$ | X |
|---|---|---|---|---|---|
| 36 | 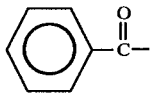 | —H | $-C_2H_5$ | $-C_2H_5$ | 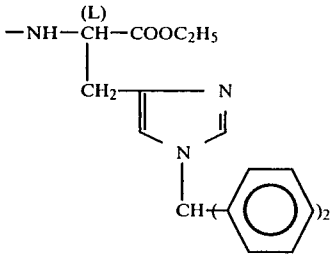 |
| 37 | 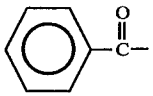 | —H | $-C_2H_5$ | $-C_2H_5$ | 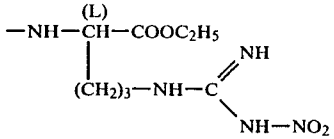 |
| 38 | 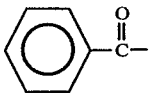 | —H | $-C_2H_5$ | $-C_2H_5$ | $-NH-CH_2-COOC_2H_5$ |
| 39 | 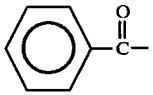 | —H | $-C_2H_5$ | $-C_2H_5$ | 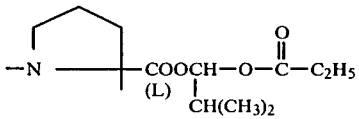 |
| 40 | 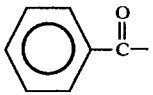 | —H | $-C_2H_5$ | $-C_2H_5$ | 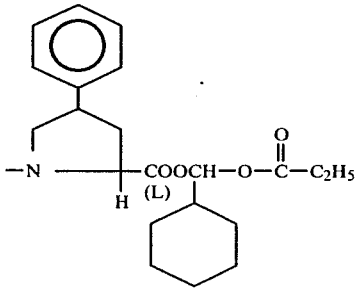 |

-continued
| Example | $R_3$ | R | $R_2$ | $R_1$ | X |
|---|---|---|---|---|---|
| 41 | 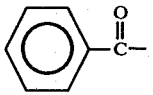 | —H | $-C_2H_5$ | $-C_2H_5$ | 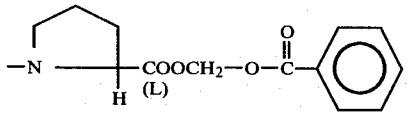 |

The $R^1$ protecting groups shown in Examples 17 to 19 and 21 and the $R_5$ protecting groups shown in Examples 35 to 37 are removed as the last step in the synthesis. The azidoproline of Example 16 when treated with a reducing agent yields a 4-aminoproline.

EXAMPLE 42

| | |
|---|---|
| 1-[[[2-(Benzoylamino)-2-carboxyethyl]ethylamino]-carbonyl]-L-proline, disodium salt (isomer A) | 100 mg. |
| Corn starch | 50 mg. |
| Gelatin | 7.5 mg. |
| Avicel(microcrystalline cellulose) | 25 mg. |
| Magnesium stearate | 2.5 mg. |
| | 185 mg. |

are prepared from sufficient bulk quantities by mixing the 1-[[[2-(benzoylamino)-2-carboxyethyl]ethylamino]-carbonyl]-L-proline, disodium salt (isomer A) and corn starch with an aqueous solution of the gelation. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 41 can be prepared.

A similar procedure can be employed to form tablets containing 50 mg. of active ingredient.

EXAMPLE 43

Two piece #1 gelatin capsules are filled with a mixture o the following ingredients:

| | |
|---|---|
| [1(R),3S]—1-[[[2-(Benzoylamino)-2-carboxyethyl]ethylamino]carbonyl]-2,3-dihydro-1H—indole-2-carboxylic acid, dilithium salt | 50 mg. |
| Magnesium stearate | 7 mg. |
| Lactose | 193 mg. |
| | 250 mg. |

In a similar manner capsules containing 50 mg. of the product of any of Examples 1 and 3 to 41 can be prepared.

EXAMPLE 44

An injectable solution is prepared as follows:

| | |
|---|---|
| 1-[[[2-(Benzoylamino)-2-carboxyethyl]ethylamino]-carbonyl]-L-proline, disodium salt (isomer A) | 500 g. |
| Methyl paraben | 5 g. |
| Propyl paraben | 1 g. |
| Sodium chloride | 5 l. |

The active substance, preservatives,and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 2 to 41.

EXAMPLE 45

1000 tablets each containing the following ingredients:

| | |
|---|---|
| [1(R),3S]—1-[[[2-(Benzoylamino)-2-carboxyethyl]-ethylamino]carbonyl]-2,3-dihydro-1H—indole-2-carboxylic acid, dilithium salt | 100 mg. |
| Avicel | 100 mg. |
| Hydrochlorothiazide | 12.5 mg. |
| Lactose | 113 mg. |
| Cornstarch | 17.5 mg. |
| Stearic Acid | 7 mg. |
| | 350 mg. |

are prepared from sufficient bulk quantities by slugging the [1(R),3S]-1-[[[2-(benzoylamino)-2-carboxyethyl]ethylamino]carbonyl]-2,3-dihydro-1H-indole-2-carboxylic acid, dilithium salt, Avicel, and a portion of the stearic acid. The slugs are ground and passed through #2 screen, then mixed with the hydrochlorothiazide lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 and 3 to 41.

What is claimed is:

1. A compound of the formula:

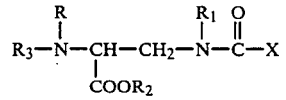

including a pharmaceutically acceptable salt thereof wherein:

X is

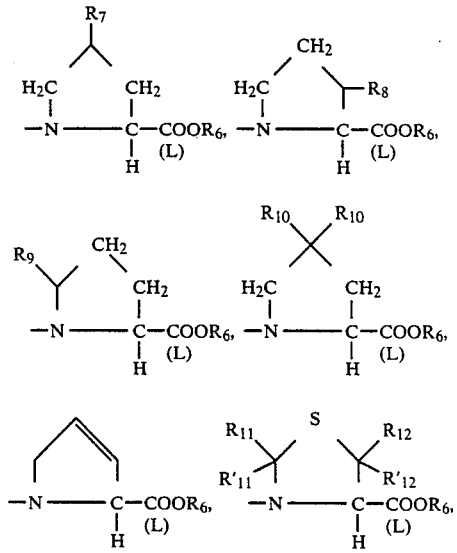

-continued
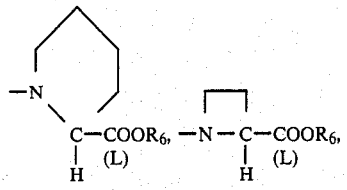
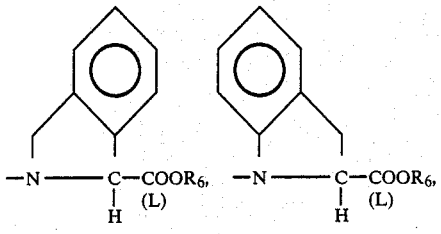
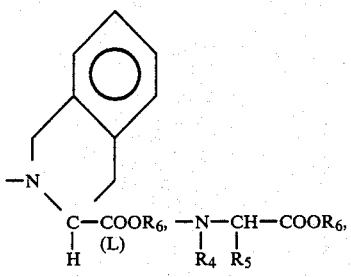
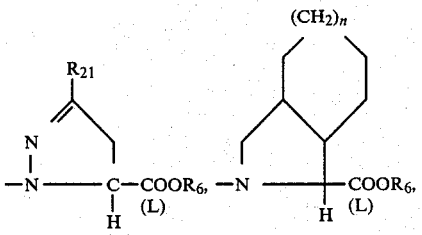
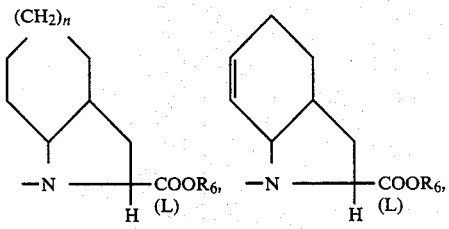
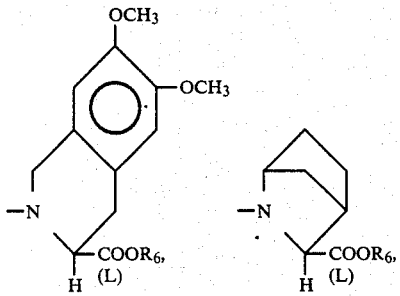
-continued
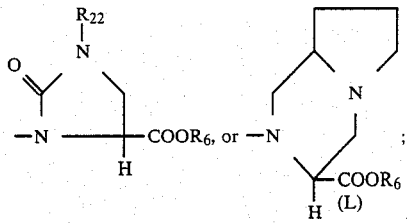
n is zero one, or two;
$R_{22}$ is lower alkyl of 1 to 4 carbons or
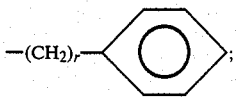
$R_7$ is hydrogen, lower alkyl, halogen, hydroxy,
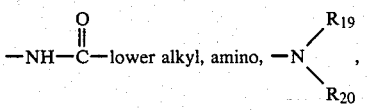
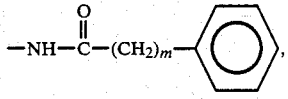
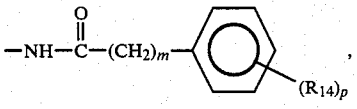
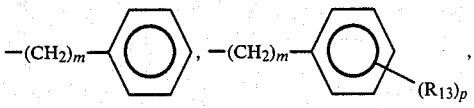
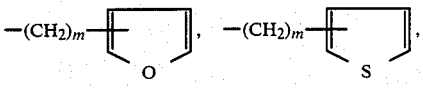
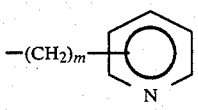
a 1- or 2-naphthyl of the formula
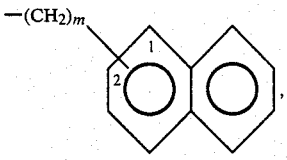
a substituted 1- or 2-naphthyl of the formula
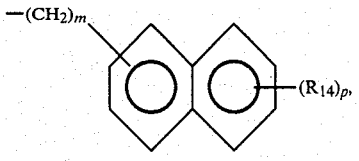

-continued

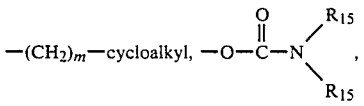

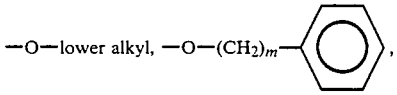

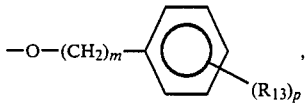

a 1- or 2-naphthyloxy of the formula

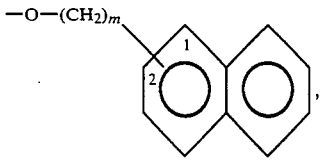

a substituted 1- or 2-naphthyloxy of the formula

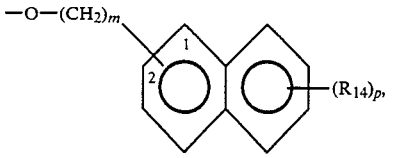

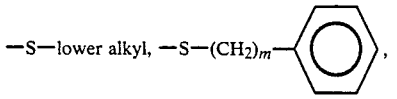

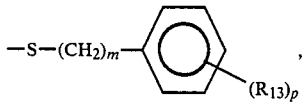

a 1- or 2-naphthylthio of the formula

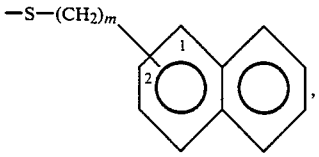

or a substituted 1- or 2-naphthylthio of the formula

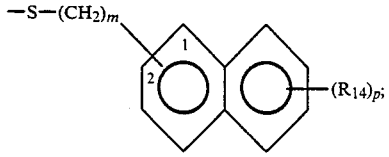

$R_8$ is halogen,

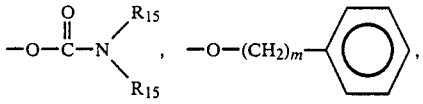

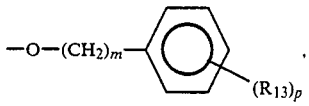

—O—lower alkyl, a 1- or 2-naphthyloxy of the formula

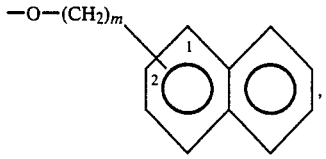

a substituted 1- or 2-napthyloxy of the formula

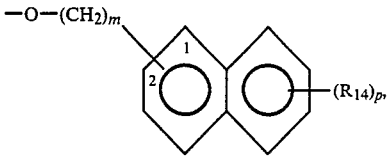

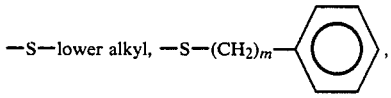

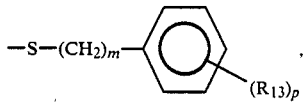

a 1- or 2-naphthylthio of the formula

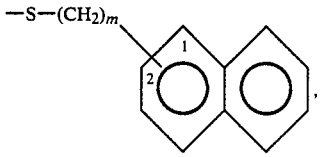

or a substituted 1- or 2-naphthylthio of the formula

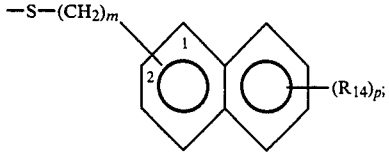

$R_9$ is keto

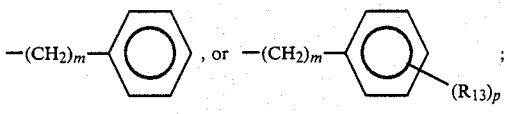

$R_{10}$ is halogen or —Y—$R_{16}$;

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

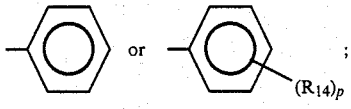

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy;

m is zero, one two, three, or four;

p is one, two or three provided that p is more than one only if $R_{13}$ or $R_{14}$ is methyl, methoxy, chloro, or fluoro ;

$R_{15}$ is hydrogen or lower alkyl of 1 to 4 carbons;

Y is oxygen or sulfur;

$R_{16}$ is lower alkyl of 1 to 4 carbons,

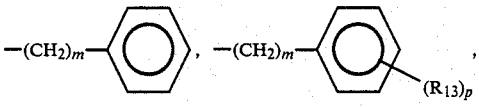

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent ;

$R_4$ is hydrogen, lower alkyl

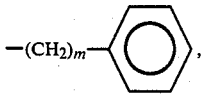

—$(CH_2)_m$—cycloalkyl,

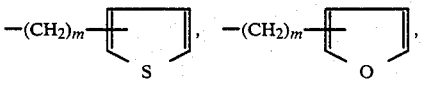

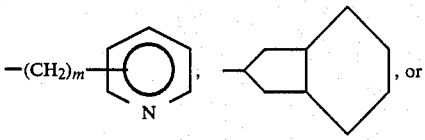

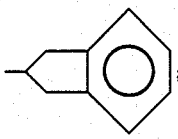

$R_5$ is hydrogen, lower alkyl,

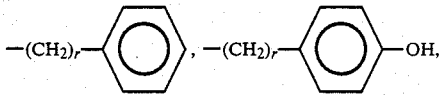

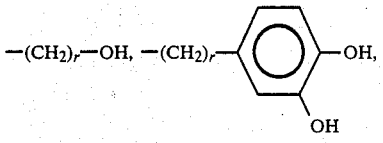

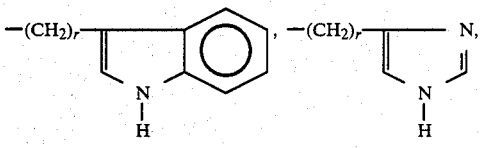

—$(CH_2)_r$—$NH_2$, —$(CH_2)_r$—SH, —$(CH_2)_r$—S—lower alkyl,

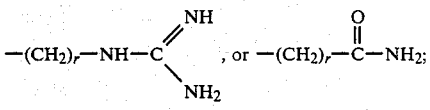

r is an integer from 1 to 4 ;

$R_{19}$ is lower alkyl, benzyl, or phenethyl;

$R_{20}$ is hydrogen, lower alkyl, benzyl or phenethyl;

$R_1$ is hydrogen, lower alkyl, halo substituted lower alkyl

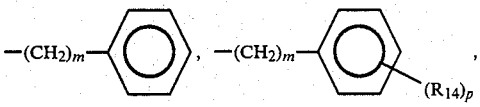

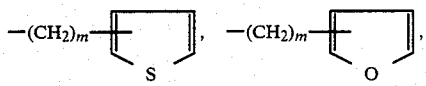

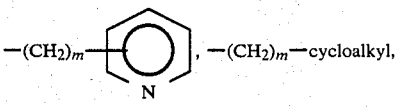

—$(CH_2)_m$—cycloalkyl,

—$(CH_2)_2$—$NH_2$, —$(CH_2)_3$—$NH_2$, —$(CH_2)_4$—$NH_2$,

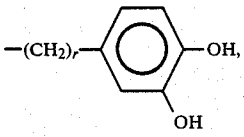

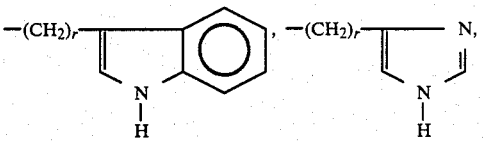

—$(CH_2)_r$—SH, —$(CH_2)_r$—OH, —$(CH_2)_r$—S—lower alkyl,

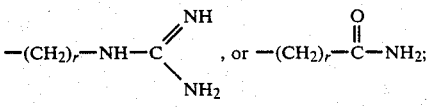

R is hydrogen, lower alkyl

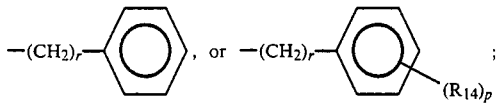

$R_3$ is hydrogen, lower alkyl,

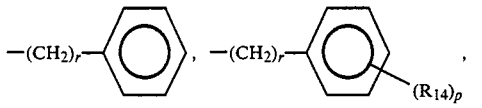

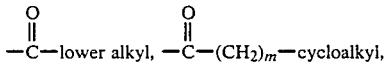

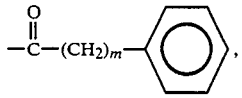

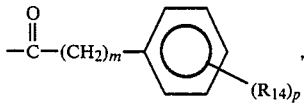

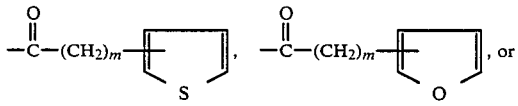

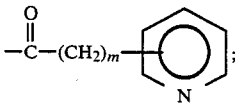

$R_2$ and $R_6$ are independently selected from hydrogen, lower alkyl, benzyl, benzhydryl,

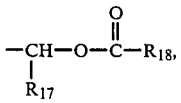

and salt forming ion;

$R_{17}$ is hydrogen, lower alkyl, cycloalkyl, or phenyl;

$R_{18}$ is hydrogen, lower alkyl, lower alkoxy, or phenyl; and $R_{21}$ is hydrogen, lower alkyl,

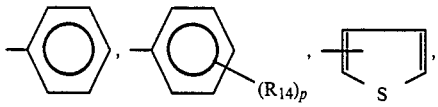

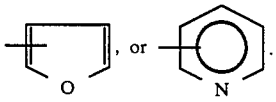

2. A compound of claim 1 wherein:

$R_2$ and $R_6$ are independently selected from the group consisting of hydrogen, straight or branched chain lower alkyl of 1 to 4 carbons, alkali metal salt ion, and

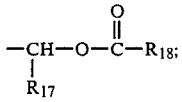

$R_4$ is hydrogen, cyclohexyl, or phenyl;

$R_5$ is hydrogen, straight or branched chain lower alkyl of 1 to 4 carbons,

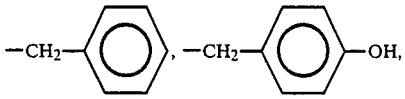

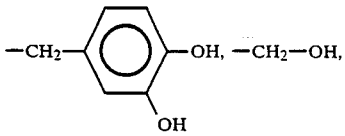

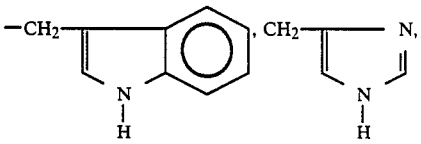

$-(CH_2)_4-NH_2$, $-CH_2-SH$, $-(CH_2)_2-S-CH_3$,

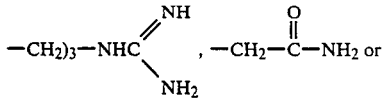

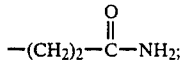

$R_{17}$ is hydrogen, straight or branched chain lower alkyl of 1 to 4 carbons, or cyclohexyl;

$R_{18}$ is straight or branched chain lower alkyl of 1 to 4 carbons or phenyl;

$R_7$ is hydrogen, hydroxy, straight or branched chain lower alkyl of 1 to 4 carbons, cyclohexyl, amino, -0-lower alkyl wherein lower alkyl is straight or branched chain of 1 to 4 carbons,

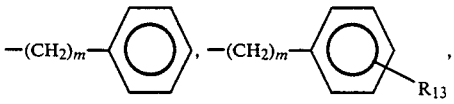

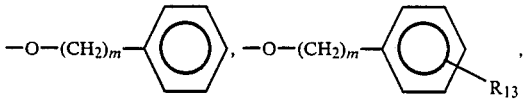

1-naphthyloxy, 2-naphthyloxy, —S-lower alkyl wherein lower alkyl is straight or branched chain of 1 to 4 carbons,

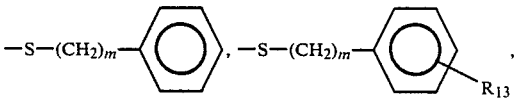

1-naphthylthio or 2-naphthylthio;

$R_8$ is —O-lower alkyl, —S-lower alkyl,

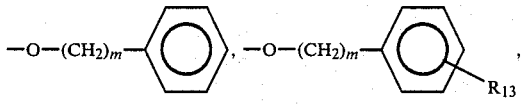

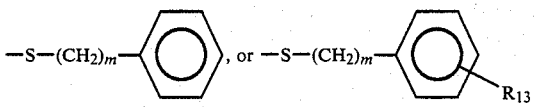

wherein lower alkyl is straight or branched chain of 1 to 4 carbons;

$R_9$ is phenyl, 2-hydroxyphenyl or 4-hydroxyphenyl;

$R_{10}$ are both fluoro, both chloro or both —Y—$R_{16}$;

Y is O or S;

$R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent;

$R_{11}$, $R_{11}'$, $R_{12}$ and $R_{12}'$ are all hydrogen or $R_{11}$ is phenyl 2-hydroxyphenyl, or 4-hydroxyphenyl and $R_{11}'$, $R_{12}$ and $R_{12}'$ are all hydrogen, m is zero, one, or two;

$R_{13}$ is methyl, methoxy, methylthio, chloro, bromo, fluoro, or hydroxy;

$R_{21}$ is phenyl;

R is hydrogen;

$R_1$ is straight or branched chain lower alkyl of 1 to 4 carbons, benzyl,

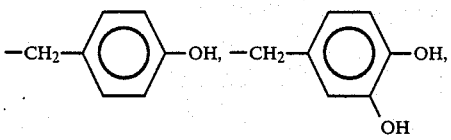

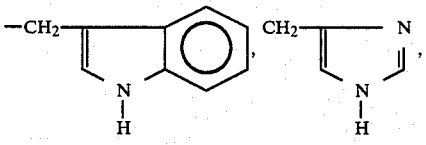

$-CH_2-SH$, $-(CH_2)_2-S-CH_3$,

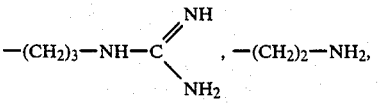

$-(CH_2)_3-NH_2$, $-(CH_2)_4-NH_2$,

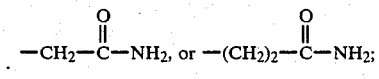

$R_3$ is

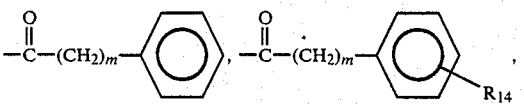

-continued

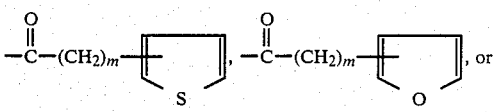

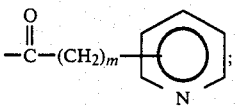

$R_{14}$ is methyl, methoxy, methylthio chloro, bromo, fluoro, or hydroxy.

3. A compound of claim 2 wherein

X is

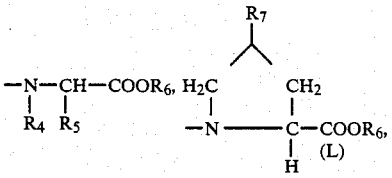

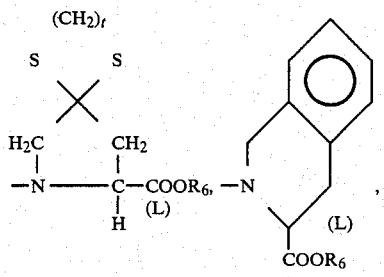

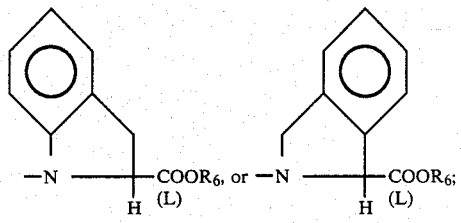

$R_2$ and $R_6$ are the same and both are hydrogen or an alkali metal salt ion;

$R_4$ is cyclohexyl or phenyl and $R_5$ is hydrogen or $R_4$ is hydrogen and $R_5$ is methyl, —$CH_2$—$CH(CH_3)_2$,

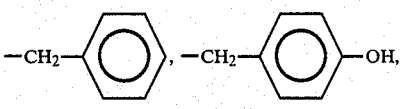

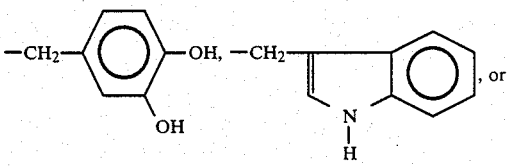

-continued

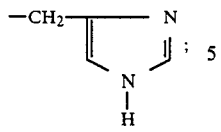

$R_7$ is hydrogen, cyclohexyl, lower alkoxy of 1 to 4 carbons,

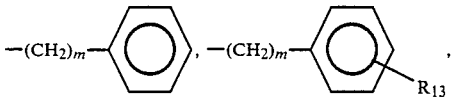

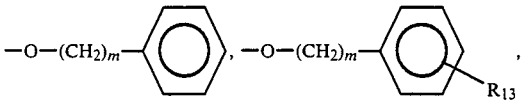

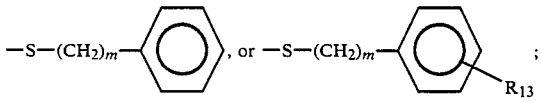

m is zero, one or two;

$R_{13}$ is methyl, methoxy, methylthio, chloro, bromo, fluoro, or hydroxy; and t is 2 or 3.

4. A compound of claim 3 wherein:

X is

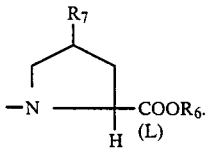

5. A compound of claim 4 wherein:

$R_3$ is

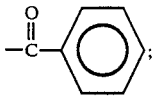

and $R_1$ is ethyl.

6. A compound of claim 5 wherein $R_7$ is hydrogen.

7. The compound of claim 6, 1-[[[2-(benzoylamino)-2-carboxyethyl]ethylamino]carbonyl]-L-proline, disodium salt.

8. A compound of claim 3 wherein

X is

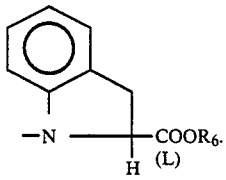

9. A compound of claim 8 wherein $R_3$ is

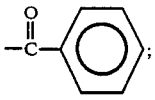

and $R_1$ is ethyl;.

10. The compound of claim 9, [1(R),3S]-1-[[[2-(benzoylamino)-2-carboxyethyl]ethylamino]carbonyl]2,3-dihydro-1H-indole-2-carboxylic acid, dilithium salt.

11. A pharmaceutical composition useful for treating hypertension comprising a pharmaceutically acceptable carrier and a hypotensive compound or pharmaceutically acceptable salt thereof of the formula

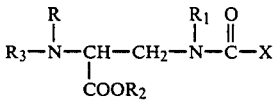

wherein X, R, $R_1$, $R_2$, and $R_3$ are as defined in claim 1.

12. The method of treating hypertension in a mammalian host which comprises administering an effective amount of the composition of claim 11.

* * * * *